Figure 1:
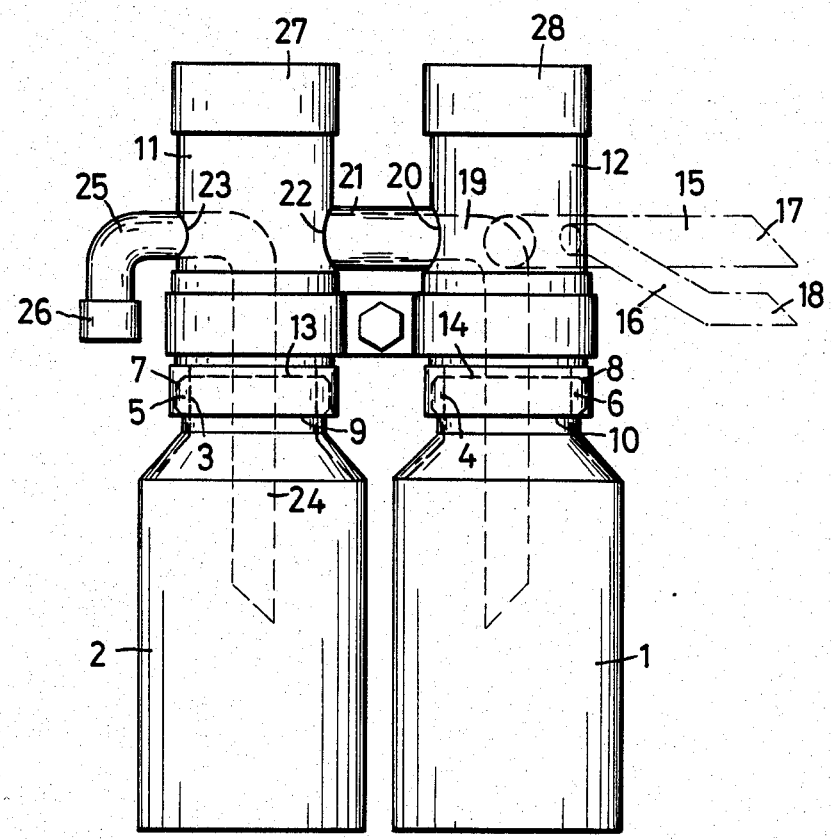

United States Patent [19]

Jerzy

[11] Patent Number: 4,529,383
[45] Date of Patent: Jul. 16, 1985

[54] GRAVITY SEPARATOR FOR USE IN DENTAL SUCTION APPARATUS

[76] Inventor: Ingo Jerzy, Am Hünengrab 11, 2056 Glinde, Fed. Rep. of Germany

[21] Appl. No.: 608,503

[22] Filed: May 9, 1984

[30] Foreign Application Priority Data

May 19, 1983 [DE] Fed. Rep. of Germany ... 8314829[U]

[51] Int. Cl.³ ............................................. A61C 17/04
[52] U.S. Cl. ....................................................... 433/92
[58] Field of Search ........................................... 433/92

[56] References Cited

U.S. PATENT DOCUMENTS 665,571 1/1901 Metzler ................................. 433/92
3,134,127 5/1964 Klein ..................................... 433/92

Primary Examiner—Robert Peshock
Attorney, Agent, or Firm—Toren, McGeady, Stanger, Goldberg & Kiel

[57] ABSTRACT

The gravity separator is intended for use in dental suction apparatus comprising at least one sucker having a suction mouthpiece and a sucker line. The suction apparatus comprises also a suction-producing machine including a pump for generating a vacuum in a suction line. The separator comprises at least two collecting containers, which are adapted to be connected in series to the at least one sucker line connected to one or more suction mouthpieces and are detachably connected to respective hollow head pieces, one of which has an inlet for connection to said at least one sucker line whereas another head piece is adapted to be connected to a suction line leading to the suction-generating machine, particularly to a pump. Each container has an open mouth leading to the associated head piece. A suction pipe extends into each container. That suction pipe which extends into the last container is connected to the suction line leading to the pump. Each of said suction pipes, except that extending into the last container, is connected above the mouth of the container to the head piece of the next following container.

17 Claims, 7 Drawing Figures

GRAVITY SEPARATOR FOR USE IN DENTAL SUCTION APPARATUS

This invention relates to a gravity separator for use in dental suction apparatus comprising at least one sucker having a suction mouthpiece and a sucker line. The suction apparatus comprises also a suction-producing machine including a pump for generating a vacuum in a suction line.

It is known from U.S. Pat. No. 3,964,114 to provide suction apparatus with a gravity separator, to which the sucker lines connected to the suction mouthpieces are connected as well as suction lines connected to pumps and a line for supplying water under pressure. The known gravity separator comprises a housing, in which a substantial turbulence is created by the supply of water under pressure, and a separation is effected in that an adequate residence time of the fluid, i.e., of the water, in contact with the particles in the container of the separator is ensured so that relatively heavy particles can settle to the bottom.

That known design involves various problems. The supply of water under pressure gives rise to turbulence, which causes suspended particles to be whirled up. It is difficult to maintain a preadjusted residence time during a suction operation which takes considerable time. For these reasons the known gravity separator is not satisfactory in operation. Filters are known too but have the disadvantage that they gradually become clogged so that a uniform action over a relatively long period is not ensured. Besides, the maintenance of filters is expensive.

It is an object of the invention so to improve a gravity separator which is of the kind described first hereinbefore that a separation of particles such as amalgam particles or gold dust or secreted matter passing through the separator will be reliably separated and the various particles will be sorted without a need for a filter. The various particles differ mainly in specific gravity and may differ also in size.

This object is accomplished in accordance with the invention in that the separator comprises at least two collecting containers, which are adapted to be connected in series to the at least one sucker line connected to one or more suction mouthpieces and are detachably connected to respective hollow head pieces, one of which has an inlet for connection to said at least one sucker line whereas another head piece is adapted to be connected to a suction line leading to the suction-generating machine, particularly to a pump, each container has an open mouth leading to the associated head piece, a suction pipe extends into each container, that suction pipe which extends into the last container is adapted to be connected to the suction line leading to the pump, and each of said suction pipes, except that extending into the last container, is connected above the mouth of the container to the head piece of the next following container. It has surprisingly been found that by the provision of a series of collecting containers the separation from a continuous stream is improved and a separate collection of different kinds of particles can be ensured so that a preliminary sorting is effected.

The collecting containers are detachably mounted so that they can easily be replaced when a predetermined quantity of particles has been collected. The containers consist preferably of transparent material so that the degree to which they have been filled can be monitored.

The suction pipe may be introduced into a container laterally and, if desired, through a separate fitting. In a preferred arrangement the suction pipe extends centrally through the mouth of the container and that mouth has a larger inside cross-section than the suction pipe extending through said mouth. In that case each container may consist of a conventional bottle having a single mouth. The centrally extending suction pipe constitutes a guiding element ensuring a uniform distribution of the entering stream throughout the periphery.

The diameter of the mouth of each container is suitably about $1\frac{1}{2}$ times the diameter of the suction pipe and the latter extends preferably centrally through said mouth. That design permits a desirable flow through the container and also permits the entering fluid to expand so that it will be stilled.

The suction pipe suitably extends in the associated upper portion of the body of the associated container through about the upper one-third of the height of said body.

To permit the separator containers to be detachably connected, each container has preferably a profiled neck, which is detachably connected to the open lower end of an associated head piece, which at said lower end has a profile that is complementary to that of the neck. The detachable connection may be established by a screwed joint, by a joint which is similar to a bayonet joint, or by similar means, so that a replacement can easily be effected.

Each head piece is desirably closed at its upper end by a detachable cap. By this feature, trouble which is due to clogging can be much more easily eliminated. Such clogging may occur when relatively large pieces, such as swabs, have been sucked through a sucker. Such large pieces will be collected in the head piece and can easily be removed from above.

In the preferred embodiment, each head piece is firmly connected to an adjacent one by a tubular extension, through which the suction pipe associated with a preceding container communicates with the head piece of the succeeding container through the mouth of the latter. Owing to that rigid arrangement, in which the parts of the separator are disposed at predetermined locations, the handling of the separator will be facilitated.

In order to effect an instantaneous stilling of flowing fluid, the bodies of the containers are suitably larger in diameter than the head pieces and are suitably also larger in diameter than the necks of the containers, which necks are detachably secured to the head pieces.

In a preferred embodiment, the containers, which are connected in series differ in volume and particularly in cross-sectional area. This feature will promote the sorting of particles of different kinds. From that aspect the suction pipes extending into the several containers may suitably differ in cross-section.

In the preferred embodiment of the gravity separator the head pieces are fixed in a housing, which is provided on its front wall with receptacles for holding suckers. Such an arrangement constitutes a compact unit, which can easily be attached to existing suction apparatus. The housing is provided on its rear side with fastening means, such as hangers provided with holes for screws.

In a preferred arrangement the housing is open-bottomed and has side walls extending below the bottoms of the containers. This design results in a closed arrangement and permits the suction lines connected to the suckers and the suction lines connected to the pump to extend out at the bottom of the housing without a need for separate feed-throughs. Moreover, the detachably mounted containers can be grasped from below and can be screwed out or removed and new containers can be inserted in case of need. Within the scope of the invention, the housing may be provided for each container of the separator with an elongated inspection opening, which preferably extends throughout the height of the container.

In accordance with another desirable feature of the invention the front part of the housing is detachably secured to a rear wall part of the housing by means of profiled portions, which constitute a joint that is similar to a bayonet joint, and the head pieces are permanently secured to said rear wall part. In that case the housing can easily be opened so that the replacement of the containers of the separator is further facilitated.

The front wall of the housing is preferably downwardly and forwardly inclined from the rear wall and the receptacles are provided on the upper portion of the front wall on a U-shaped handle. By means of that U-shaped handle, the front part of the housing can be manipulated when that front part is to be removed.

Figure 3:
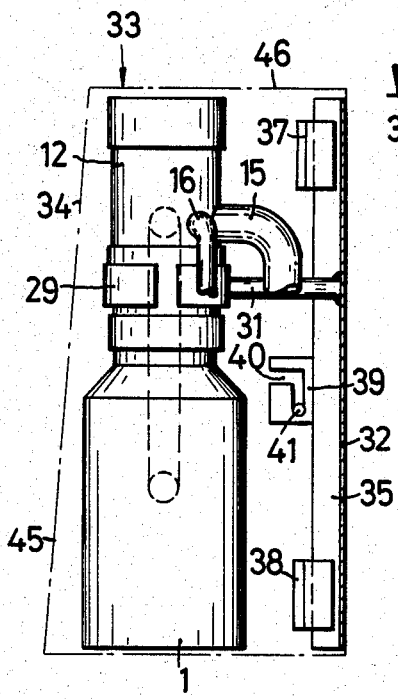
Figure 2:
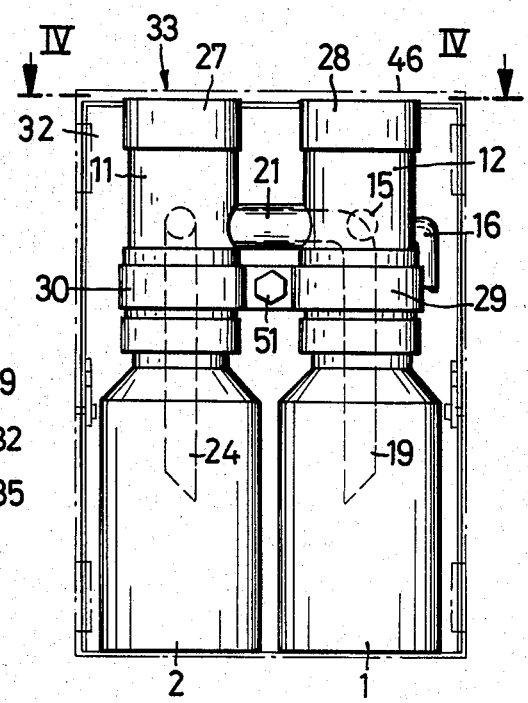
Figure 4:
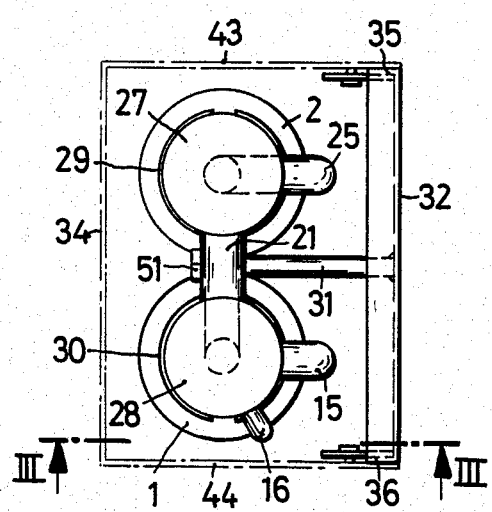
Figure 6:
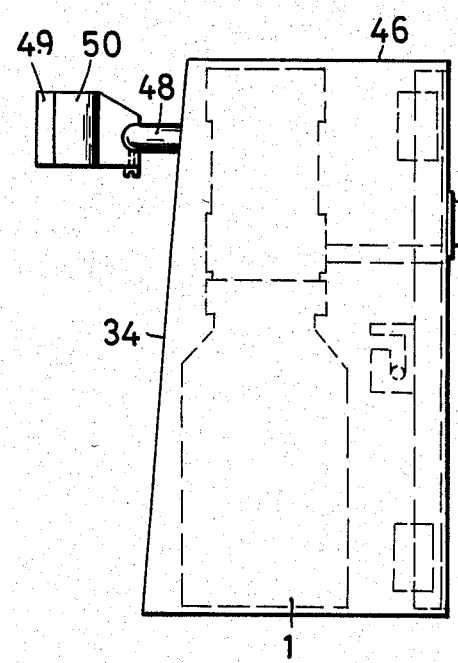
Figure 5:
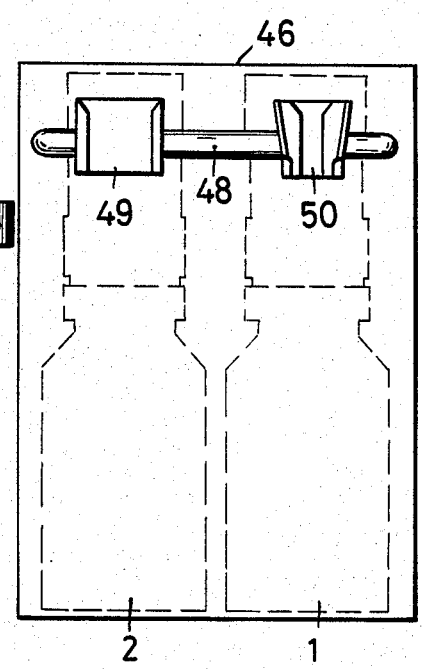
Figure 7:
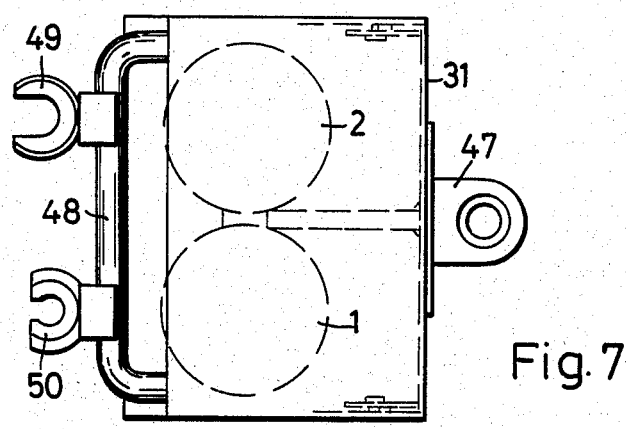

The invention will now be explained with reference to illustrative embodiments, which are shown on the drawing, in which FIG. 1 is a diagrammatic side elevation showing a gravity separator having two containers, FIG. 2 is a front elevation showing a housing from which the front part has been omitted, for an explanation of a separator as shown in FIG. 1, FIG. 3 is a vertical sectional view taken on line III—III in FIG. 4, FIG. 4 shows the housing in a horizontal sectional view taken on line IV—IV in FIG. 2, FIG. 5 is a front elevation showing the housing and indicates the internally disposed collecting containers only by dotted lines, FIG. 6 is a side elevation showing the housing of FIG. 5 and FIG. 7 is a top plan view showing the housing of FIGS. 5 and 6.

In the basic embodiment shown in FIG. 1 the gravity separator comprises closely spaced collecting containers 1, 2, which are connected in series in the flow path and consist, e.g., of bottles of glass or another suitable material. As is known for bottles, each container has a neck 3 or 4, which is profiled on the outside, e.g., formed with screw threads 5 or 6, which have been screwed into female screw threads 7 or 8 in an opening 9 or 10 of a hollow head piece 11 or 12. The screw threads may be replaced by other interengaging profiled portions, e.g., parts which constitute a joint that is similar to a bayonet joint. The collecting containers 1, 2 are detachably connected to the open-bottomed head pieces 11, 12 in such a manner that a seal is obtained, e.g., between the lower rim of each head piece and the shoulder with which each container is formed around its neck. A sealing ring may be provided at the rim of each lower opening 9 or 10. In the embodiment shown, the neck of each collecting container 1 or 2 has an open mouth 13 or 14.

Two sucker lines 15, 16 connected to respective suction mouthpieces 17, 18 open into the preferably cylindrical shell of the head piece 12. The suction mouthpieces 17, 18 differ in cross-section and may belong to a so-called mist sucker and a so-called saliva sucker. It is apparent that the sucker lines open into the head piece on an intermediate level so that the volume of the head piece contributes to the expansion of the entering flowing fluid.

Approximately at the middle of the height of the head piece 12, an angled suction pipe 19 is secured to the wall of the head piece 12 and extends through the mouth 14 into the collecting container 1 and terminates in the upper portion of the body of said container. That wall opening at which the suction pipe 19 terminates is connected by a fixed tubular extension 21 to the head piece 11 which is associated with the following container. That tubular extension terminates in an opening 22, which is disposed approximately in the middle of the height of the head piece. The latter has on a lower level an opening 23, at which an angled suction pipe 24 is secured, which extends centrally through the mouth 13 into the collecting container 2 and through the upper portion of the body of said collecting container. Each of the two suction pipes 19 and 24 is provided at its lower end with an opening, which is preferably inclined relative to the longitudinal axis of the lower end portion of the suction pipe so that the opening is larger in cross-section. On the outside of the head piece 11, a suction line 25 extends from the opening 23 and is provided with a fitting 26 for connection to the suction machine or pump for generating the vacuum to be applied to the suction mouthpieces 17, 18.

Each head piece 11, 12 is closed at its top rim with a detachable cap 27, 28 so that the head piece is accessible from above when it is to be cleaned. It is apparent that each collecting container 1, 2 can easily be unscrewed.

In the following figures of the drawings, like parts are designated with the same reference characters.

It is apparent that the two head pieces 11, 12, which are connected by the tubular extension, are secured by means of retaining clips 29, 30 and an intermediate carrier 31 to the rear wall part 32 of a housing, which is generally designated 33. The retaining clips 29, 30 can be opened by means of a screw 51 so that the head pieces can be removed.

A front part 34 of the housing 33 is detachably secured to the rear wall part 32. In the embodiment shown by way of example, the rear wall part has forwardly angled edge portions 35, 36, which are received at the top and bottom in angle brackets 37, 38 secured to a side wall of the front part 34 of the housing and in their middle portion carry a bracket 39, which is formed with an L-shaped slot 40, which is adapted to receive an inwardly protruding pin 41 or 42, which is provided on each side wall 43 or 44 of the front part of the housing.

The front part of the housing consists of the side walls 43 and 44, a front wall 45 and a top cover 46. The housing 33 is open at its bottom so that the lines can extend out of the housing at its bottom. Through the open bottom the containers 1 and 2 can also be screwed out. The front part of the housing can easily be removed so that the caps 27, 28 can be taken off.

FIGS. 5 to 7 show another feature of the housing which has been described hereinbefore. A bracket 47 is secured to the rear wall part 31 and is used to attach the housing to a machine. The downwardly protruding front wall 34 is provided at its top with a U-shaped handle 48, at which the front part of the housing can be grasped and which is provided with receptacles 49, 50 for the suction mouthpieces 17, 18.

What is claimed is:
1. In a gravity separator for dental suction apparatus comprising a suction line, at least one suction mouth- piece and at least one sucker line connected between said at least one suction mouthpiece and said suction line, the improvement residing in that said gravity separator comprises a plurality of collecting containers, each of which has an open mouth and is provided with connecting means, a plurality of hollow head pieces, each of which is associated with one of said collecting containers and is detachably connected thereto by said connecting means and communicates with said associated container through said open mouth thereof, one of said head pieces constituting a first head piece and has at least one inlet opening for connection to said at least one sucker line, each remaining one of said head pieces having an inlet opening, each of said head pieces having an outlet opening, and a plurality of suction pipes, each of which extends from one of said containers through said open mouth thereof into the head piece associated with said container and to said outlet opening of said head piece, one of said suction pipes being adapted to be connected to said suction line and each remaining one of said suction pipes communicating with said inlet opening of a remaining one of said head pieces.

2. The improvement set forth in claim 1, wherein each of said suction pipes extends centrally through and is larger in cross-sectional area than said open mouth of the associated container.

3. The improvement set forth in claim 2, wherein said open mouth of each of said containers and each of said suction pipes are circular in cross-section and said open mouth of said container has a diameter which is about one and a half times the diameter of the suction pipe extending through said open mouth.

4. The improvement set forth in claim 1, wherein each of said containers has a lower portion and an upper portion, which defines said open mouth and is provided with said connecting means and is smaller in cross-sectional area than said lower portion, and each of said suction pipes depends into the associated container through about the upper one-third of the height of said lower portion.

5. The improvement set forth in claim 1, wherein each of said containers has at its top a neck, which is provided with a profiled portion, which constitutes said connecting means, and each of said head pieces has at its lower end an opening and near said opening is provided with a profiled portion, which is complementary to and detachably connected to said profiled portion of the associated container.

6. The improvement set forth in claim 1, wherein a cap is detachably mounted on the upper end of each of said head pieces.

7. The improvement set forth in claim 1, wherein a tubular extension is rigidly connected to each remaining one of said head pieces and extends from the inlet opening thereof to the outlet opening of another one of said head pieces, with the exception of the outlet opening through which said one suction pipe extends, said tubular extension being rigidly connected to said other head piece, and each remaining one of said suction pipes communicates with a remaining one of said head pieces through said tubular extension and communicates with the container associated with said remaining one of said head pieces through the open mouth of said container.

8. The improvement set forth in claim 1, wherein each of said containers has a lower portion, which is circular in cross-section, and each of said head pieces is circular in cross-section and smaller in diameter than said lower portion of the associated container.

9. The improvement set forth in claim 1, wherein each of said containers has an upper portion, which defines said mouth and is provided with said connecting means and is circular in cross-section and smaller in diameter than said lower portion of said container.

10. The improvement set forth in claim 1, wherein one of said containers differs in volumetric capacity from another one of said containers.

11. The improvement set forth in claim 1, wherein each of said containers has a lower portion, which is larger in cross-sectional area than the head piece associated with said container, and the lower portions of different ones of said containers differ in cross-sectional area.

12. The improvement set forth in claim 1, wherein the lower portion of one of said containers differs in cross-sectional area from the lower portion of another one of said containers.

13. The improvement set forth in claim 1, wherein one of said suction pipes differs in cross-sectional area from another one of said suction pipes.

14. The improvement set forth in claim 1, wherein said containers, head pieces and suction pipes are accommodated in an open-bottomed housing, said head pieces are secured to said housing, said housing has a wall provided on the outside with receptacles for holding said suction mouthpieces of said dental suction apparatus, and said housing has side walls extending below the lower ends of said containers.

15. The improvement set forth in claim 14, wherein said housing comprises a front part and a rear part, said head pieces are secured to said rear part, and said front and rear parts are interconnected by profiled elements forming a joint which is similar to a bayonet joint.

16. The improvement set forth in claim 14, wherein said housing comprises a rear wall and a front wall, which is forwardly and downwardly inclined from and protrudes downwardly from said rear wall, and a U-shaped handle is carried by said front wall on an upper portion thereof and carries said receptacles.

17. The improvement set forth in claim 1, wherein each of said suction pipes has a lower end portion depending into the associated container and having at its lower end an opening, which is inclined from the longitudinal axis of said lower end portion.

* * * * *